(12) United States Patent
Li et al.

(10) Patent No.: US 11,241,381 B2
(45) Date of Patent: Feb. 8, 2022

(54) TREATMENT PROCESS OF CYCLOSPORINE EYE GEL

(71) Applicant: ZHAOKE (GUANGZHOU) OPHTHALMIC DRUG COMPANY LIMITED, Guangzhou (CN)

(72) Inventors: Gang Li, Hefei (CN); Kailei Cao, Hefei (CN); Xiaoyi Li, Hong Kong (HK); Xiangrong Dai, Hefei (CN); Lei Yin, Hefei (CN); Juan Ling, Hefei (CN)

(73) Assignee: ZHAOKE (GUANGZHOU) OPHTHALMIC DRUG COMPANY LIMITED, Guangzhou (CN)

(*) Notice: Subject to any disclaimer, the term of this patent is extended or adjusted under 35 U.S.C. 154(b) by 0 days.

(21) Appl. No.: 16/231,973

(22) Filed: Dec. 25, 2018

(65) Prior Publication Data

US 2019/0192426 A1    Jun. 27, 2019

(30) Foreign Application Priority Data

Dec. 26, 2017    (CN) .......................... 201711427891.9

(51) Int. Cl.
| | | |
|---|---|---|
| *A61K 9/00* | (2006.01) |
| *A61K 38/13* | (2006.01) |
| *A61K 47/10* | (2017.01) |
| *A61K 47/32* | (2006.01) |
| *A61K 47/44* | (2017.01) |
| *A61K 9/107* | (2006.01) |
| *A61K 9/06* | (2006.01) |

(52) U.S. Cl.
CPC .............. *A61K 9/0048* (2013.01); *A61K 9/06* (2013.01); *A61K 9/107* (2013.01); *A61K 38/13* (2013.01); *A61K 47/10* (2013.01); *A61K 47/32* (2013.01); *A61K 47/44* (2013.01)

(58) Field of Classification Search
None
See application file for complete search history.

(56) References Cited

U.S. PATENT DOCUMENTS

| 8,258,132 B2 * | 9/2012 | Bosch ..................... A61K 9/145 514/231.5 |
| 2011/0229517 A1 * | 9/2011 | Strahlendorf .......... A61K 39/00 424/204.1 |
| 2018/0207230 A1 * | 7/2018 | Blanda .................... A61P 37/08 |

FOREIGN PATENT DOCUMENTS

| CN | 101810563 | * | 4/2012 |
| CN | 103735495 | A | 4/2014 |
| CN | 103735495 | * | 7/2016 |
| CN | 105726479 | A | 7/2016 |
| CN | 106692052 | A | 5/2017 |

OTHER PUBLICATIONS

English translation of CN 101810563 (Nov. 2019).*
English translation of CN 103735495 (Nov. 2019).*

* cited by examiner

*Primary Examiner* — Patricia Duffy
*Assistant Examiner* — Garen Gotfredson
(74) *Attorney, Agent, or Firm* — Bayramoglu Law Offices LLC

(57) ABSTRACT

A treatment process of cyclosporine eye gel, comprising the steps of: adding carbomer to water, stirring thoroughly and homogenizing; after the prepared carbomer base swollen, stirring and homogenizing; cooling the carbomer base after moist heat sterilization, performing vacuum degassing, adjusting the pH of the base to 5.0-9.0 with filtered sodium hydroxide solution; mixing polyoxyl 35 castor oil, cyclosporin A raw material, 1,2-propanediol and water in a suitable ratio, preparing into a clear solution under a water bath at 35 to 45° C., and filtering; mixing the filtrate uniformly with the carbomer base, performing vacuum degassing; performing aseptic filling after another filtration. For the process of the present invention, sterilization and filtration is performed before adding carbomer, which is convenient for industrial production.

10 Claims, No Drawings

TREATMENT PROCESS OF CYCLOSPORINE EYE GEL

CROSS REFERENCE TO THE RELATED APPLICATIONS

This application is based upon and claims priority to Chinese Patent Application No. CN201711427891.9, filed on Dec. 26, 2017, the entire contents of which are incorporated herein by reference.

TECHNICAL FIELD

The present invention relates to the field of medicine, in particular to a treatment process of cyclosporine eye gel.

BACKGROUND

Cyclosporin A is a cyclic peptide containing 11 amino acids extracted from fungi and is a third-generation high-efficiency immunosuppressant for the treatment of dry eye.

For ophthalmic preparations, the state requires management according to the injection, so the sterility guarantee of the preparation is critical. At present, there are three main aspects of sterility guarantee: sterilization filtration process, aseptic process and terminal sterilization process. Cyclosporine is poorly soluble and thermally unstable, so cyclosporine aseptic preparation is a problem.

At present, the following three methods are mainly used for aseptic processing: procurement of sterile raw materials and operation in a sterile environment; end product moist heat sterilization; terminal product sterilization process. For the first method, it is difficult to purchase qualified sterile raw materials, and the preparation process and workshop environment are all sterile, rendering that the production cost is high, and the difficulty is high. For the second method end product moist heat sterilization, although the preparation can be guaranteed to be sterilized and operation is also better, but cyclosporine itself is not resistant to high temperature, which causes cyclosporine to produce more degradation impurities, increase the safety risk of the preparation, and produce side effects. For the third method terminal product sterilization process, it can only be used in the process of small-scale trials, is difficult to commercial production because the emulsion gel has a high viscosity and is easy to block a filter with small pore size, and the filtration is slow, and the production efficiency is difficult to ensure.

Patent No. CN201410033737.3 "A cyclosporine eye gel and its preparation method" discloses use of moist heat sterilization to ensure sterility. It is found via reproducible detection that moist heat sterilization causes cyclosporine to produce degradation impurities.

Patent No. CN201510785005.4 "a cyclosporine ophthalmic emulsion composition" relates to a formulation of a sterile raw material and an auxiliary material, which is industrially difficult to apply. Patent No. CN201610172271.4 "Cyclosporine Ophthalmic Emulsion" uses a configured emulsion terminal for sterilization filtration. It is difficult for a viscous emulsion to pass a 0.22 micron sterile filter, so it is not feasible. In summary, the various aseptic processes currently disclosed do not have the value and feasibility of commercial production.

SUMMARY

One of the purposes of the present invention is to address the sterility of cyclosporine ophthalmic high risk formulations.

In view of this, the present invention provides a cyclosporin A eye gel treatment process comprising the following steps:

Step 1: adding carbomer to water, stirring thoroughly and homogenizing; after the prepared carbomer base swollen, stirring and homogenizing;

Step 2: cooling the base after moist heat sterilization, performing vacuum degassing, adjusting the pH of the base to 5.0-9.0 with filtered sodium hydroxide solution;

Step 3: mixing castor oil polyoxyl ester (35), cyclosporin A raw material, 1,2-propanediol and water in a suitable ratio, preparing into a clear solution under a water bath at 35 to 45° C., and filtering;

Step 4: mixing the filtrate uniformly and the base obtained in the step 2, performing vacuum degassing; performing aseptic filling after another filtration.

Preferably, the swelling time in step 1 is 12-24 hours;

Preferably, the moist heat sterilization in step 2 is sterilized at 115-121° C. for 15-90 min. More preferably, the moist heat sterilization in step 2 is sterilized at 117° C. for 31 min.

Preferably, the carbomer in step 1 is carbomer 981.

Preferably, the cooling in step 2 is to a temperature below 40° C.; the pH of the substrate in step 2 is preferably 7.0.

Preferably, the filtration in step 2 is filtered through a 0.2 um polyethersulfone capsule filter.

Preferably, the clear solution of step 3 is prepared at 35-45° C. More preferably, the clear solution is prepared in a 40° C. water bath.

Preferably, the mass ratio of carbomer to water is from 3:4500 to 5500.

Preferably, the mass ratio of the castor oil polyoxyl ester (35), cyclosporin A raw material, 1,2-propanediol, and water is 20-30:1-2:44-48:64-68.

More preferably, the filtration in step 3 is filtration with a capsule filter of 0.2 um PVDF; the filtration in step 4 is filtration with a 20 um polypropylene capsule filter.

Compared with the prior art, it has the following advantages:

1. For the process of the present invention, sterilization and filtration is performed before adding cyclosporine to the carbomer, and the viscosity of the filter medium is small compared to the terminal sterilization process of the final product, which is convenient for industrial production;

2. The process of the present invention only needs partial sterility, and the sterility requirement for the raw materials is low compared with the use of the sterilized raw materials in the whole aseptic environment, which is convenient for procurement and cost reduction;

3. Compared with the terminal sterilization, the process of the present invention can avoid the thermal degradation of cyclosporine, reduce product impurities and provide safety.

The process of the invention significantly improves the production efficiency, and only takes 50,000 hours for 20,000 pieces; multiple batches of products produced were aseptically qualified and uniformly transparent.

The process of the invention has high filtration efficiency, less adsorption, suitable viscosity of the preparation, which has a significant influence on the efficacy of the preparation. The preparation prepared by the process of the present invention is qualified for various indexes such as appearance, identification, pH, osmotic pressure, viscosity, content uniformity, content, related substances and sterility, suggesting good industrial application prospects.

DETAILED DESCRIPTION OF THE EMBODIMENTS

The present invention discloses a treatment process of a cyclosporine eye gel, and those skilled in the art can learn from the contents disclosed herein and appropriately improve the process parameters. It is to be understood that all such replacements and modifications are obvious to those skilled in the art and are considered to be included in the present invention. The method of the present invention has been described in terms of preferred examples, and it is obvious that the method and application described herein may be changed or modified and combined to implement and apply the present invention without departing from the content, spirit, and scope of the present invention.

In order to make those skilled in the art better understand the technical embodiments of the present invention, the present invention will be further described in detail below with reference to specific examples.

Example 1

Cyclosporine A Eye Gel Process
1. Preparation of carbomer 981 base:
(1) adding an appropriate amount of water for injection into a liquid mixing tank, adding the prescribed amount of carbomer 981, stirring and homogenizing;
(2) adding an appropriate amount of water for injection to the liquid mixing tank, stirring and homogenizing;
(3) allowing the base stand and swell, wherein the swelling time is 12 h;
(4) turning on the equipment, stirring and homogenizing;
(5) performing moist heat sterilization at 115° C. for 80 min, while stirring and circulating, cooling the base to below 40° C., and performing vacuum degassing;
2. pH adjustment: adjusting the pH of the base with sodium hydroxide solution to 6.0, continuing to stir for an appropriate time;
3. Addition of cyclosporine A solution and the sterilization filter to the liquid mixing tank:
(1) Weighing the prescribed amount of castor oil polyoxyl ester (35) and heating in a hot water bath for a few minutes, then slowly adding the prescribed amount of cyclosporine A raw material, while stirring, until cyclosporine A raw material completely dissolved under a hot water bath, and adding the prescribed amount of 1,2-propanediol, heating in hot water bath and stirring until clarification, adding an appropriate amount of water for injection under water bath at 35° C., and stirring until clarification (in which castor oil polyoxyl ester (35):cyclosporine A raw material:1,2-propanediol:water for injection=15:1:24:34), the time required is 30 minutes, which is long;
(2) Adding (1) using a capsule filter of 0.2 um PES via a peristaltic pump to the liquid mixing tank;
4. Mixing, stirring and weighing to the total amount of batch production;
6. Mixing and stirring time for 20 minutes;
7. Vacuuming and degassing for 30 minutes;
8. Sampling of intermediates to detect pH, viscosity, osmotic pressure, related substances and content;
9. Passing the intermediate through a 30 um polypropylene capsule filter for aseptic filling.

Example 2

Cyclosporine A Eye Gel Process
1. Preparation of carbomer 981 base:
(1) Adding an appropriate amount of water for injection into a liquid mixing tank, adding a prescribed amount of carbomer 981, stirring and homogenizing;
(2) Adding an appropriate amount of water for injection to the liquid mixing tank, stirring and homogenizing;
(3) Allowing the base stand and swell, wherein the swelling time is 19 h;
(4) Turning on the equipment, stirring and homogenizing;
(5) Performing moist heat sterilization of the base at 117° C. for 31 min, while stirring and circulating, cooling the base to below 40° C., and performing vacuum degassing;
2. pH adjustment: adjusting the pH of the base with sodium hydroxide solution to 7.0, continuing to stir for a few minutes;
3. Addition of cyclosporine A solution and the sterilization filter to the liquid mixing tank:
(1) Weighing the prescribed amount of castor oil polyoxyl ester (35) and heating it in a hot water bath for a few minutes, then slowly adding the prescribed amount of cyclosporine A raw material, while stirring, until cyclosporine A raw material completely dissolved under a hot water bath, and adding the prescribed amount of 1,2-propanediol, heating under hot water bath and stirring until clarification, and adding an appropriate amount of water for injection under the water bath at 40° C., and stirring until clarification (in which castor oil polyoxyl ester (35)):cyclosporine A raw material:1,2-propanediol:water for injection=20:1:44:64), the required time is 10 min, less time than the example 1, which saves time;
(2) Adding (1) using a capsule filter of 0.2 um PVDF via a peristaltic pump to the liquid mixing tank;
4. Mixing, stirring and weighing to the total amount of batch production;
6. Mixing and stirring for 20 minutes;
7. Performing vacuum degassing for 30 minutes;
8. Sampling of intermediates to detect pH, viscosity, osmotic pressure, related substances and content;
9. Passing the intermediate through a 20 um polypropylene capsule filter for aseptic filling.

Example 3

Cyclosporine a Eye Gel Process
1. Preparation of carbomer 981 base:
(1) Adding an appropriate amount of water for injection into a liquid mixing tank, adding a prescribed amount of carbomer 981, stirring and homogenizing;
(2) Adding an appropriate amount of water for injection to the liquid mixing tank, stirring and homogenizing;
(3) Allowing the base stand and swell, wherein the swelling time is 24 hours;
(4) Turning on the equipment, stirring and homogenizing;
(5) Performing moist heat sterilization of the base at 121° C. for 20 min, while stirring and circulating, cooling the base to below 40° C., and performing vacuum degassing;
2. pH adjustment: adjusting the pH of the base with sodium hydroxide solution to 9.0, continuing to stir for a few minutes;
3. Addition of cyclosporine A solution and the sterilization filter to the liquid mixing tank:
(1) Weighing the prescribed amount of castor oil polyoxyl ester (35) and heating it in a hot water bath for 15 min, then slowly adding the prescribed amount of cyclosporine A raw material, while stirring, until cyclosporine A raw material completely dissolved under a hot water bath, and adding the prescribed amount of 1,2-propanediol, heating under hot water bath and stirring until clarification, and adding an appropriate amount of water for injection under the water bath at 45° C., and stirring until clarification (in which castor oil polyoxyl ester (35)):cyclosporine A raw material:1,2-propanediol:water for injection=25:1.5:46:66), the required time is 8 min, which is comparable to example 2;

(2) Adding (1) using a capsule filter of 0.2 um polypropylene via a peristaltic pump to the liquid mixing tank;

4. Mixing, stirring and weighing to the total amount of batch production;

6. Mixing and stirring for 20 minutes;

7. Performing vacuum degassing for 30 minutes;

8. Sampling intermediates to detect pH, viscosity, osmotic pressure, related substances and content;

9. Passing the intermediate through a 20 um polypropylene capsule filter for aseptic filling.

Example 4

Cyclosporine A Eye Gel Process

1. Preparation of carbomer 981 base:

(1) Adding an appropriate amount of water for injection into a liquid mixing tank, adding a prescribed amount of carbomer 981, stirring and homogenizing;

(2) Adding an appropriate amount of water for injection to the liquid mixing tank, stirring and homogenizing;

(3) Allowing the base stand and swell, wherein the swelling time is 24 hours;

(4) Turning on the equipment, stirring and homogenizing;

(5) Performing moist heat sterilization of the base at 121° C. for 20 min, while stirring and circulating, cooling the base to below 40° C., and performing vacuum degassing;

2. pH adjustment: adjusting the pH of the base with sodium hydroxide solution to 9.0, continuing to stir for a few minutes;

3. Addition of cyclosporine A solution and the sterilization filter to the liquid mixing tank:

(1) Weighing the prescribed amount of castor oil polyoxyl ester (35) and heating it in a hot water bath, then slowly adding the prescribed amount of cyclosporine A raw material, while stirring, until cyclosporine A raw material completely dissolved under a hot water bath, and adding the prescribed amount of 1,2-propanediol, heating under hot water bath and stirring until clarification, and adding an appropriate amount of water for injection under the water bath at 45° C., and stirring until clarification (in which castor oil polyoxyl ester (35)):cyclosporine A raw material:1,2-propanediol:water for injection=25:1.5:46:66), the required time is 8 min, which is comparable to example 2;

(2) Adding (1) using a capsule filter of 0.2 um polypropylene via a peristaltic pump to the liquid mixing tank;

4. Mixing, stirring and weighing to the total amount of batch production;

6. Mixing and stirring for 20 minutes;

7. Performing vacuum degassing for 30 minutes;

8. Sampling intermediates to detect pH, viscosity, osmotic pressure, related substances and content;

9. Passing the intermediate through a 20 um polypropylene capsule filter for filling until the clogging of the filter and the termination of production.

Example 5

Detection Results of Various Indexes of Cyclosporine Eye Gel Prepared by the Process of the Present Invention

| detection result | Example 1 | Example 2 | Example 3 |
| --- | --- | --- | --- |
| appearance | colorless transparent gel, with visual particulate matter | colorless transparent gel | colorless transparent gel |
| pH value | 6.14 | 6.87 | 9.06 |
| related substances (total impurities) | 1.47 | 1.06 | 1.65 |
| content | 80.6% | 100.7% | 90.8% |
| osmotic pressure | 0.367 smol/kg | 0.304 smol/kg | 0.331 smol/kg |
| viscosity | 161.4 cp | 181.8 cp | 164.9 cp |
| content uniformity | 12.14 | 7.00 | 14.28 |
| Asepsis | comply with regulations | comply with regulations | comply with regulations |

As can be seen from Examples 1, 2 and 3, Example 2 is an optimum process.

The above examples are only preferred embodiments of the present invention, and it should be noted that those skilled in the art can also make several improvements and modifications without departing from the principles of the present invention. These improvements and modifications should also be considered within the scope of protection of the present invention.

What is claimed is:

1. A treatment process of a cyclosporin A eye gel, comprising the steps of:
    Step 1: adding carbomer to water to obtain a first mixture, stirring thoroughly and homogenizing the first mixture to obtain a first carbomer base, and after the first carbomer base swells to obtain a second carbomer base, stirring and homogenizing the second carbomer base;
    Step 2: performing a moist heat sterilization of the second carbomer base after the second carbomer base is stirred and homogenized, cooling the second carbomer base, performing a vacuum degassing on the second carbomer base to obtain a third carbomer base, and adjusting a pH of the third carbomer base to be 5.0-9.0 via addition of a filtered sodium hydroxide solution;
    Step 3: mixing polyoxyl 35 castor oil, cyclosporin A raw material, 1,2-propanediol and water to prepare a clear solution under a water bath at 35° C. to 45° C., and filtering the clear solution to obtain a filtered clear solution; and
    Step 4: mixing the filtered clear solution uniformly with the third carbomer base after the pH of the third carbomer is adjusted to 5.0-9.0 in Step 2 to obtain a second mixture, performing a vacuum degassing, filtering the second mixture, and performing an aseptic filling on the second mixture after the second mixture is filtered.

2. The treatment process according to claim 1, wherein in the Step 1, a mass ratio of the carbomer and the water is from 3:4500 to 5500 and a swelling time is from 12 hours to 24 hours.

3. The treatment process according to claim 1, wherein in the Step 2, the moist heat sterilization is performed at 115° C.-121° C. for 15-90 min.

4. The treatment process according to claim 1, wherein in the Step 2, the moist heat sterilization is performed at 117° C. for 31 min.

5. The treatment process according to claim 1, wherein in the Step 2, the filtered sodium hydroxide solution is obtained by filtering a sodium hydroxide solution through a 0.2 um capsule filter made of polyethersulfone.

6. The treatment process according to claim 1, wherein in the Step 2, the pH of the third carbomer base is adjusted to 7.0.

7. The treatment process according to claim 1, wherein in the Step 3, the clear solution is prepared in the water bath at 40° C.

8. The treatment process according to claim 1, wherein in the Step 3, a mass ratio of the polyoxyl 35 castor oil, the cyclosporin A, the 1,2-propanediol and the water is 20-30:1-2:44-48:64-68.

9. The treatment process according to claim 1, wherein in the Step 3, the clear solution is filtered by using a 0.2 μm capsule filter made of polyvinylidene fluoride.

10. The treatment process according to claim 1, wherein in the Step 4, the second mixture is filtered by using a 20 μm capsule filter made of polypropylene.

\* \* \* \* \*